US009724211B1

(12) United States Patent
Snell

(10) Patent No.: US 9,724,211 B1
(45) Date of Patent: Aug. 8, 2017

(54) PROSTHETIC DEVICES HAVING ELECTRONIC DISPLAY AND METHODS OF FABRICATION THEREOF

(71) Applicant: Christopher C. Snell, Shreveport, LA (US)

(72) Inventor: Christopher C. Snell, Shreveport, LA (US)

( * ) Notice: Subject to any disclaimer, the term of this patent is extended or adjusted under 35 U.S.C. 154(b) by 0 days.

(21) Appl. No.: 13/909,799

(22) Filed: Jun. 4, 2013

(51) Int. Cl.
*A61F 2/80* (2006.01)
*A61F 2/68* (2006.01)
*A61F 2/70* (2006.01)
*A61F 2/50* (2006.01)

(52) U.S. Cl.
CPC .................. *A61F 2/68* (2013.01); *A61F 2/80* (2013.01); *A61F 2002/5056* (2013.01); *A61F 2002/6881* (2013.01); *A61F 2002/707* (2013.01)

(58) Field of Classification Search
CPC .. A61F 2/5046; A61F 2/54; A61F 2/68; A61F 2/80; A61F 2002/7695; A61F 2/64; A61F 2002/5056; A61F 2002/6881; A61F 2002/769
USPC ........ 623/24–27, 32–37, 57–65, 901; 2/905; 362/103
See application file for complete search history.

(56) References Cited

U.S. PATENT DOCUMENTS

| 3,319,317 A | 5/1967 | Roche et al. |
| 5,413,611 A | 5/1995 | Haslam, II et al. |
| 5,443,525 A | 8/1995 | Laghi |
| 5,448,999 A | 9/1995 | Teare et al. |
| 5,573,501 A | 11/1996 | Ruscito et al. |
| 5,766,825 A | 6/1998 | Shirai et al. |
| 5,779,735 A * | 7/1998 | Molino ........................ 623/44 |
| 6,391,138 B1 | 5/2002 | Bablee et al. |
| 7,094,058 B2 | 8/2006 | Einarsson |
| 7,273,538 B2 | 9/2007 | Chen et al. |
| 7,375,609 B2 | 5/2008 | Suzuki et al. |
| 2004/0034436 A1* | 2/2004 | Einarsson ..................... 623/24 |
| 2006/0198121 A1* | 9/2006 | Thorpe et al. ............... 362/103 |
| 2007/0213839 A1* | 9/2007 | Nachbar ....................... 623/26 |
| 2011/0078888 A1* | 4/2011 | Horkey ......................... 29/458 |
| 2012/0249505 A1* | 10/2012 | Pietro et al. ................. 345/208 |
| 2013/0079693 A1* | 3/2013 | Ranky et al. ................. 602/28 |
| 2013/0190669 A1* | 7/2013 | Rokosz et al. ............... 602/16 |

OTHER PUBLICATIONS

Gator Glass. Grace Prosthetic Fabrication. (Ad) Dec. 2012. oandp. com.*
Flash Lights. North Sea Plastics Ltd. Verified by the Wayback Machine Nov. 25, 2012.*
D-Day. Oct. 21, 2007. (See figure labeled ilimb test socket).*
Man gets smartphone dock built into prosthetic arm. The Telegraph. Oct. 25, 2011. (See the figure.).*
Clark, Sarah. HTC unveils NFC remote control for Butterfly smartphone. Jan. 28, 2013. NFO World.*

(Continued)

*Primary Examiner* — Thomas J Sweet
*Assistant Examiner* — Christie Bahena
(74) *Attorney, Agent, or Firm* — R. Keith Harrison

(57) ABSTRACT

A prosthetic device includes a prosthesis wall, at least one display carried by the prosthesis wall in spaced-apart relationship to the at least one display and interfacing with the at least one display, the control module adapted to present at least one image on the at least one display.

8 Claims, 12 Drawing Sheets

(56) References Cited

OTHER PUBLICATIONS

Nguyen, Chuong. New case allows iphone owners to show 'PDA' Aug. 8, 2011. Gottoabe Mobile.*
The Telegraph. Man gets smartphone dock built into prosthetic arm. Oct. 25, 2011.*
Advanced Arm Dynamics (1, 2). Wesley Thompson. Public/open facebook page. Apr. 27, 2012.*
Advanced Arm Dynamics Ipod. Apr. 16, 2012. Public Facebook Page.*
Iron Man Hand. May 2, 2013. Xrobots.co.uk.*
Carroll, Kevin (1, 2). Prosthetics and Patient Management. p. 80. Copyright 2006.*
D-Day. Oct. 21, 2007. A one handed blog. http://onehandedblogger.wordpress.com/tag/recovery/.*
Beambox MiLi Evolution Projector. Projector Central. Verified by the Wayback Machine Apr. 10, 2010.*
LGG4 (Nokia C7). GSM Arena. Sep. 2010.*
MacKenzie, Craig. How to Laminate Sockets. O&P Edge. Jun. 2011.*

* cited by examiner

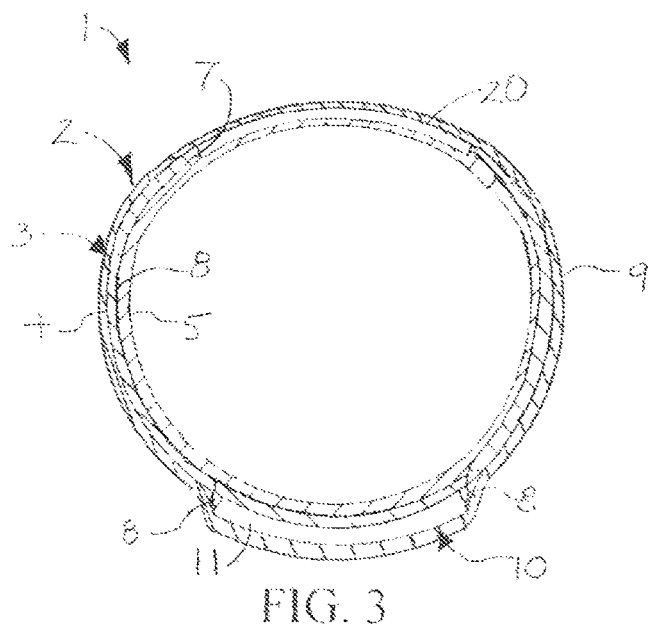
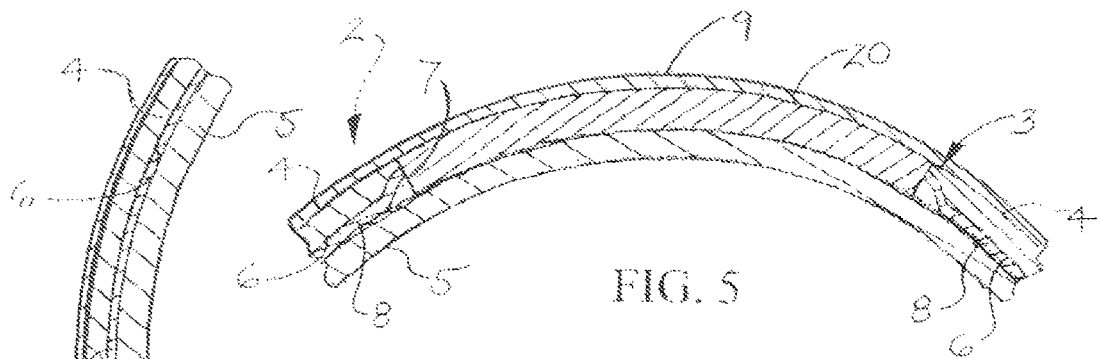
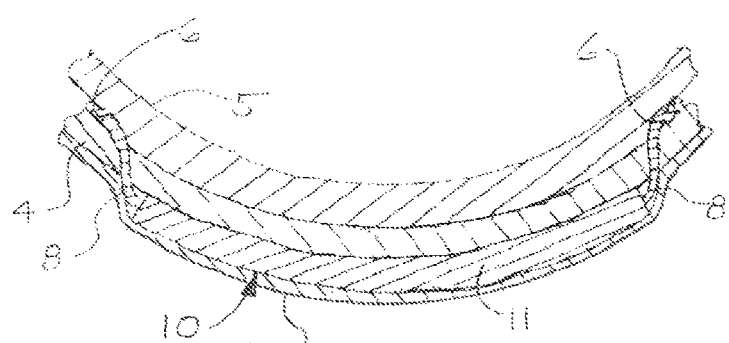
FIG. 3
FIG. 4
FIG. 5
FIG. 6

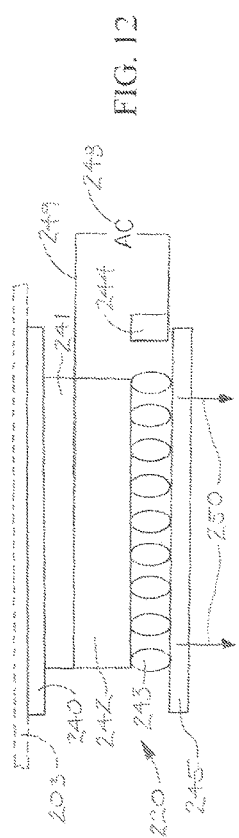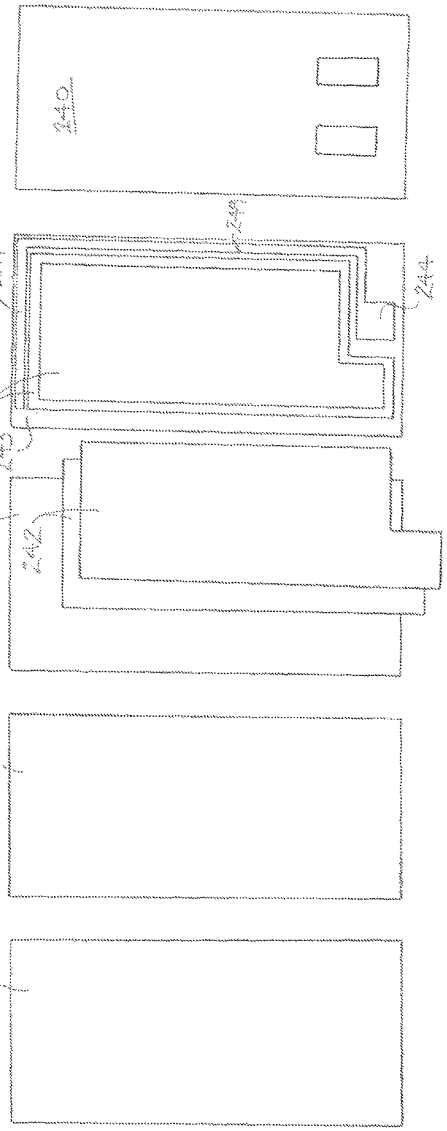

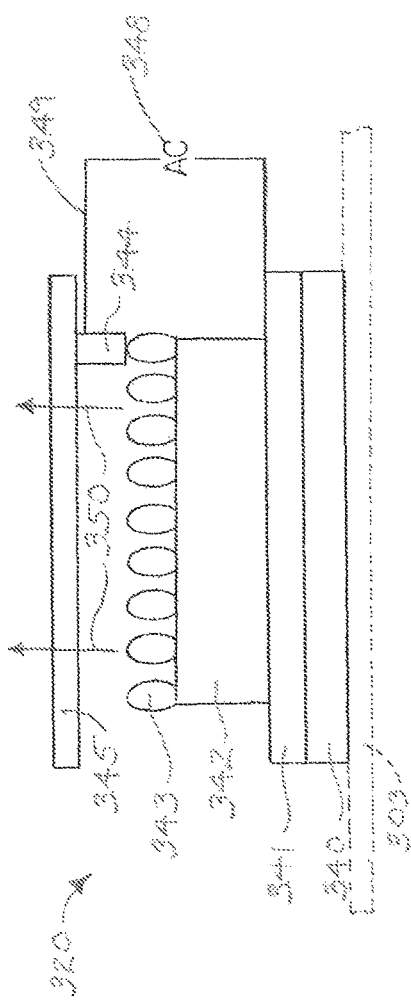
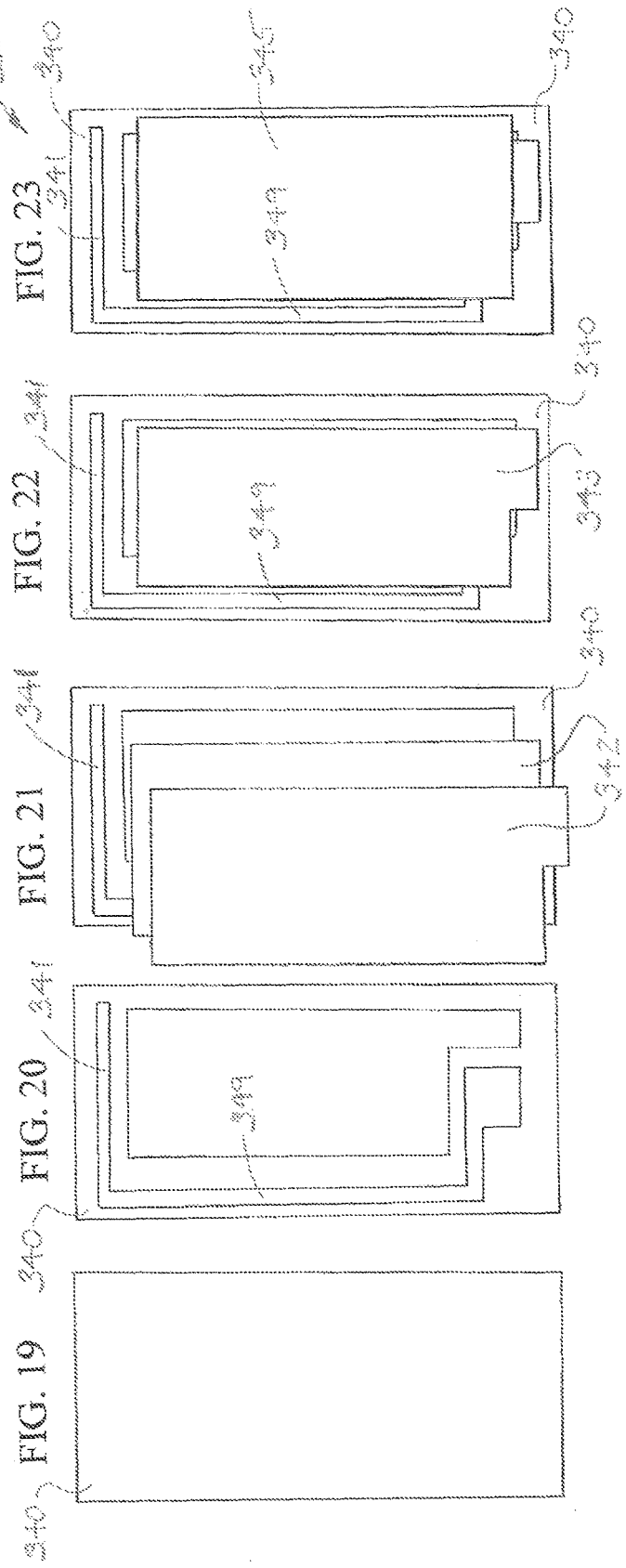

PROSTHETIC DEVICES HAVING ELECTRONIC DISPLAY AND METHODS OF FABRICATION THEREOF

CROSS-REFERENCE TO RELATED APPLICATIONS

This application claims the benefit of U.S. provisional application No. 61/555,012, filed Jun. 4, 2012 and entitled PROSTHETIC DEVICES HAVING ELECTRONIC DISPLAY AND METHODS OF FABRICATION THEREOF, which provisional application is incorporated by reference herein in its entirety.

FIELD

Illustrative embodiments of the disclosure are generally directed to prosthetic devices. More particularly, illustrative embodiments of the disclosure are directed to prosthetic devices having at least one electronic display and methods of fabricating prosthetic devices having at least one electronic display.

BACKGROUND

Prosthetic devices include prosthetic arms and legs which are worn by persons who have lost or are missing a limb due to accident, disease or congenital deformity. Conventional prosthetic devices are typically fabricated to simulate the appearance and function of natural limbs. For example, a prosthetic arm may include a hand having mechanical fingers and an opposable mechanical thumb that can perform a grasping action. Prosthetic legs may enable a wearer to ambulate in a normal manner.

Conventional prosthetic devices are typically designed to simulate the appearance of natural limbs as closely as possible. However, many persons having a prosthetic limb may desire to express themselves by customization of the appearance of their prosthetic limbs. This customization may include the display of various images on the prosthetic limb.

Accordingly, prosthetic devices having at least one electronic display by which a wearer of a device can express himself or herself using images on the display, and methods of fabricating prosthetic devices having at least one electronic display, may be desirable for some applications.

SUMMARY

The disclosure is generally directed to a prosthetic device. An illustrative embodiment of the prosthetic device includes a prosthesis wall, a display carried by the prosthesis wall and a control module carried by the prosthesis wall in spaced-apart relationship to the display and interfacing with the display, the control module adapted to present at least one image on the display.

The disclosure is further generally directed to a method of fabricating a prosthetic device. An illustrative embodiment of the method includes forming a positive model; placing an interior sheet/layer over the positive model; placing a wiring sheet/layer having control module wiring over the interior sheet/layer; placing an exterior sheet/layer over the wiring sheet/layer; distributing resin through the interior sheet/layer, the wiring sheet/layer and the exterior sheet/layer; curing the resin; connecting a display to the control wiring in the wiring sheet/layer; and connecting a control module to the control wiring in the wiring sheet/layer.

BRIEF DESCRIPTION OF THE DRAWINGS

Illustrative embodiments of the disclosure will now be made, by way of example, with reference to the accompanying drawings, in which:

FIG. 3 is a cross-sectional view of the illustrative prosthetic device illustrated in FIG. 1;

FIG. 4 is an enlarged sectional view of a side wall portion of the illustrative prosthetic device;

FIG. 5 is an enlarged sectional view of a front wall portion of the illustrative prosthetic device, with an exemplary display provided on the front wall portion;

FIG. 6 is an enlarged sectional view of a rear wall portion of the illustrative prosthetic device with an exemplary control module provided on the rear wall portion;

FIG. 12 is a cross-sectional diagram which illustrates an exemplary electroluminescent display according to an illustrative embodiment of the prosthetic devices with electronic display;

FIGS. 13-17 illustrate an exemplary sequential fabrication technique for the electroluminescent display illustrated in FIG. 12;

FIG. 18 is a cross-sectional diagram which illustrates an alternative exemplary electroluminescent display according to an illustrative embodiment of the prosthetic devices with electronic display;

FIGS. 19-23 illustrate an exemplary sequential fabrication technique for the electroluminescent display illustrated in FIG. 18.

DETAILED DESCRIPTION

Figure 1:
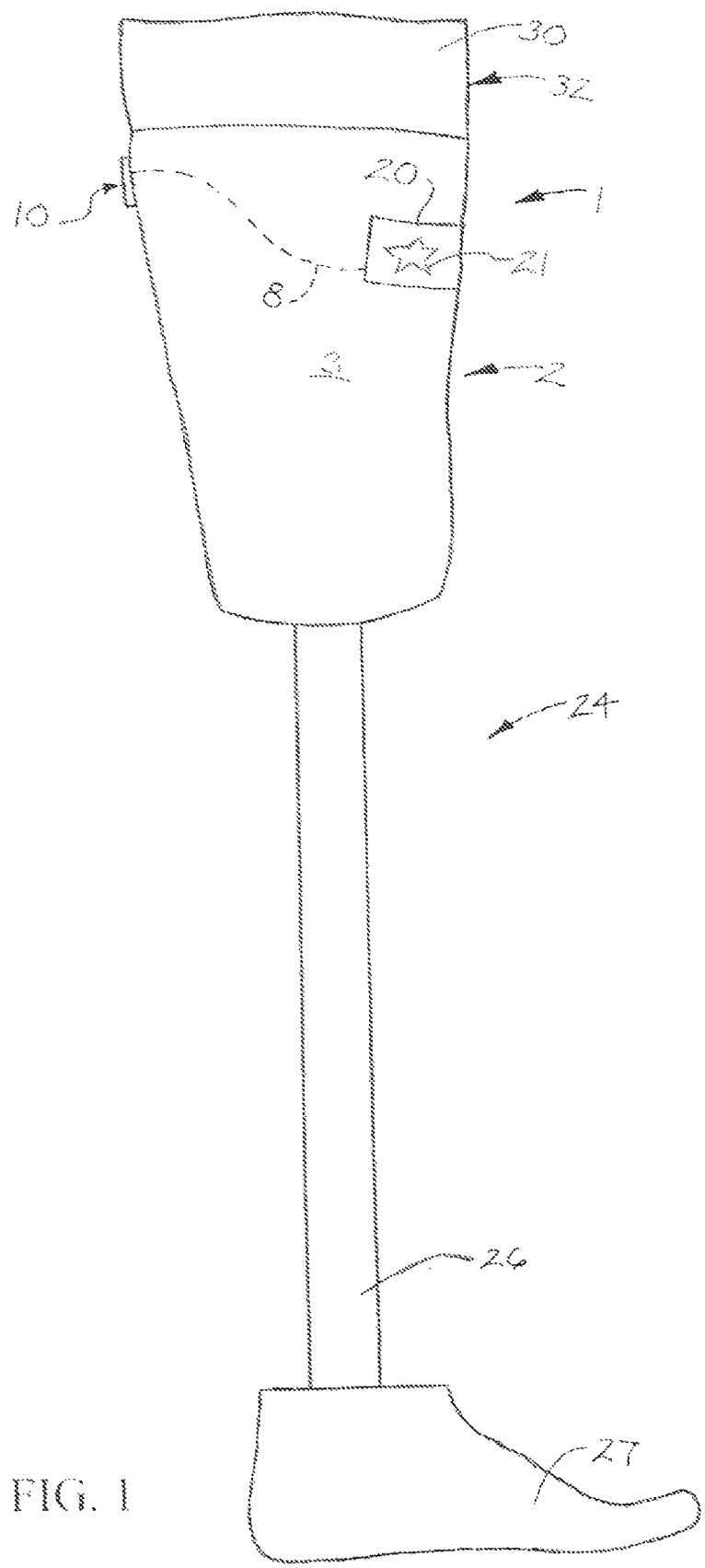
FIG. 1 is a side view of an illustrative leg embodiment of the prosthetic devices with electronic display, fitted on the leg (illustrated in section) of a wearer.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Moreover, the illustrative embodiments described herein are not exhaustive and embodiments or implementations other than those which are described herein and which fall within the scope of the appended claims are possible. Furthermore, there is no intention to be bound by any expressed or implied theory presented in the preceding technical field, background, brief summary or the following detailed description. As used herein, relative terms such as "upper", "lower", "front" and "back" are used to describe exemplary positions of various components relative to each other in exemplary use of the prosthetic devices and are not intended to be construed in a limiting sense.

Referring initially to FIGS. 1-6 of the drawings, an illustrative embodiment of the prosthetic devices having electronic display, hereinafter prosthetic device, is generally indicated by reference numeral 1. The prosthetic device 1 may be designed to be fitted on the residual limb 30 below the knee, as illustrated, or alternatively, on the residual limb above the knee (not illustrated) of a wearer 32 to replace a portion of or most of the wearer's natural limb which was lost or is missing due to injury, illness or congenital deformity, for example. In some embodiments, the prosthetic device 1 may include an upper leg portion 2 which receives the residual limb 30 of the wearer 32. A lower leg portion 24 may include a support pylon 26 which extends from the upper leg portion 2. In the case of an above the knee prosthesis, the lower leg portion 24 may include a knee component (not illustrated). A foot portion 27 may be provided on the support pylon 26. It will be recognized and understood that the prosthetic device 1 which is illustrated in FIGS. 1-6 is merely one example of a prosthetic device design which is suitable for implementation of the prosthetic device 1.

As will be hereinafter further described, at least one display 20 is provided on or in at least one of the upper leg portion 2 and the lower leg portion 24 of the prosthetic device 1. In some embodiments, the display may be provided on the front, side and/or rear portion of the upper leg portion 2. A control module 10 may be connected to each display 20, such as via control wiring 8, and/or via wireless signals 29 (FIGS. 9A), for example and without limitation, for selective control of the display 20, as will be hereinafter described. The control wiring 8 may be embedded in a prosthesis wall 3 of the prosthetic device 1. In some embodiments, the control module 10 may be attached to the exterior surface of the upper leg portion 2 or the lower leg portion 24. In other embodiments, the control module 10 may be embedded inside the lamination of the prosthesis wall 3, the support pylon 26 or a wireless transmitter (not illustrated) which is part of the control module 10, for example and without limitation. Techniques which are suitable for attaching the control module 10 to the prosthesis wall 3 include but are not limited to hook and loop fasteners, magnets, brackets, adhesives and mechanical fasteners. In other embodiments, the control module 10 may be recessed in a control module recess, cavity or void (not illustrated) provided in the exterior surface or lamination of the upper leg portion 2 or the lower leg portion 24.

As illustrated in FIGS. 3-5, the upper leg portion 2 (and/or the lower leg portion 24 in some embodiments) may have a generally annular prosthesis wall 3. The prosthesis wall 3 may include an outer wall sheet/layer 4 and an inner wall sheet/layer 5. Each of the outer wall sheet/layer 4 and the inner wall sheet/layer 5 of the prosthesis wall 3 may be fabricated using materials and methods which are well-known in the fabrication of prosthetic devices. For example and without limitation, the outer wall sheet/layer 4 and the inner wall sheet/layer 5 may include plastic, fiberglass, carbon fiber and/or other material which is fabricated on a mold (not illustrated) from multiple sheet/layers of woven reinforced and non-reinforced materials and a curable plastic resin material, as is known by those skilled in the art. In some embodiments, at least one coating layer 9 may be provided on the outer wall layer 4. The coating layer 9 may include at least one clear coating and/or sealing layer which may coat the outer wall layer 4, the control module housing 11 of the control module 10 and the display 20. The outer wall sheet/layer 4, the inner wall sheet/layer 5 and the coating layer 9 of the prosthesis wall 3 can be applied using any technique which is known by those skilled in the art and is consistent with the material of construction of each layer. These application techniques include but are not limited to silk screening, screen printing, painting and spraying.

As illustrated in FIGS. 4-6, a wiring space 6 may be provided in the prosthesis wall 3. The wiring space 6 may be formed between the outer wall sheet/layer 4 and the inner wall sheet/layer 5. In some embodiments, the wiring space 6 may accommodate the control wiring 8 as the control wiring 8 extends from the control module 10 to the display 20. In some embodiments, a display cavity 7 may be provided in the outer surface of the prosthesis wall 3. The display cavity 7 may be sized and configured to accommodate the display 20, as will be hereinafter described. In some embodiments, it may be desirable to position the display 20 in a highly-visible location and the control module 10 in a less visible location on the prosthesis wall 3. For example and without limitation, in some embodiments, the display 20 and the control module 10 may be provided at the front and rear, respectively, of the prosthesis wall 3, in substantially opposite or 180-degree relationship to each other on opposite sides of the upper leg portion 2 or the lower leg portion 24. In other embodiments, the relative positions of the display 20 and the control module 10 may be reversed. Accordingly, the control wiring 8 may extend from the control module 10 to the display 20 through the wiring space 6 on opposite sides of the prosthesis wall 3. In some embodiments, the display cavity 7 may be omitted and the display 20 may be attached to the exterior surface of the prosthesis wall 3 according to the knowledge of those skilled in the art.

Figure 9:
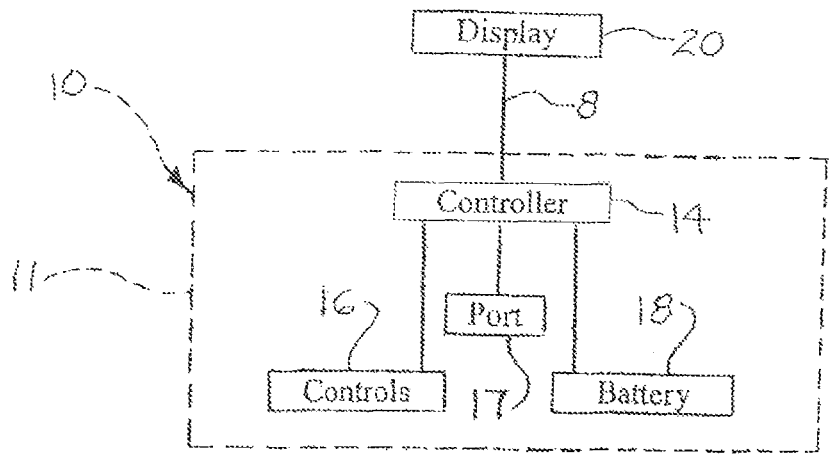
FIG. 9 is a block diagram of an exemplary control module and a display connected to the control module according to an illustrative embodiment of the prosthetic devices with electronic display.

As illustrated in FIG. 9, in some embodiments, the control module 10 may include a control module housing 11. The control module housing 11 may have any desired shape. In some embodiments, the control module housing 11 may have a concave surface which is generally complementary to the convex curvature of the exterior surface of the prosthesis wall 3. A microprocessor, CPU or other controller, hereinafter controller 14, may be provided in the control module housing 11. Display controls 16 and at least one battery 18 may electrically interface with the controller 14. The display 20 may be connected to the controller 14 through the control wing 8. In some embodiments, at least one solar panel (not illustrated) may interface with the controller 14 or with the battery 18 to provide a source of electrical power.

The controller 14 may be adapted to present at least one image 21 (FIG. 1) on the display 20. The image 21 may include a favorite sports team emblem, a business logo, a slogan, a symbol and/or any other image or images which a wearer of the prosthetic device 1 desires to display on the display 20. The image 21 may include a static image (an unchanging size, shape and/or color) and/or a dynamic image (a changing size, shape and/or color) and may be a single color or various colors. In some embodiments, the controller 14 may be adapted to present multiple images 21 in the form of video, animation and/or other visual effects on the display 20. In some embodiments, the display 20 may include an LCD (Liquid Crystal Display), LED (Light Emitting Diode) or AOLED (Active Organic Light Emitting Diode) screen, for example and without limitation. In other embodiments, the display 20 may include at least one electric light which is formed or shaped into the desired image 21 to be displayed.

As further illustrated in FIG. 9, in some embodiments, at least one port 17 such as a standard USB port or other type of port interfaces with the controller 14 and is provided on the exterior of the control module housing 11 and may be wireless in some embodiments. The controller 14 may be loaded with software, code or other programming which enables the wearer 32 to upload selected image and/or video data files from an external device (not illustrated) to the controller 14 via the port 17 such as in the conventional manner. The controller 14 may be programmed to present or display images and/or video encoded by the loaded image or video data files on the display 20 by manipulation of the appropriate display controls 16 on the control module 10. In some embodiments, the control module 10 and the display 20 may be retrofitted to an existing prosthetic device 1 according to the knowledge of those skilled in the art.

Figure 9A:
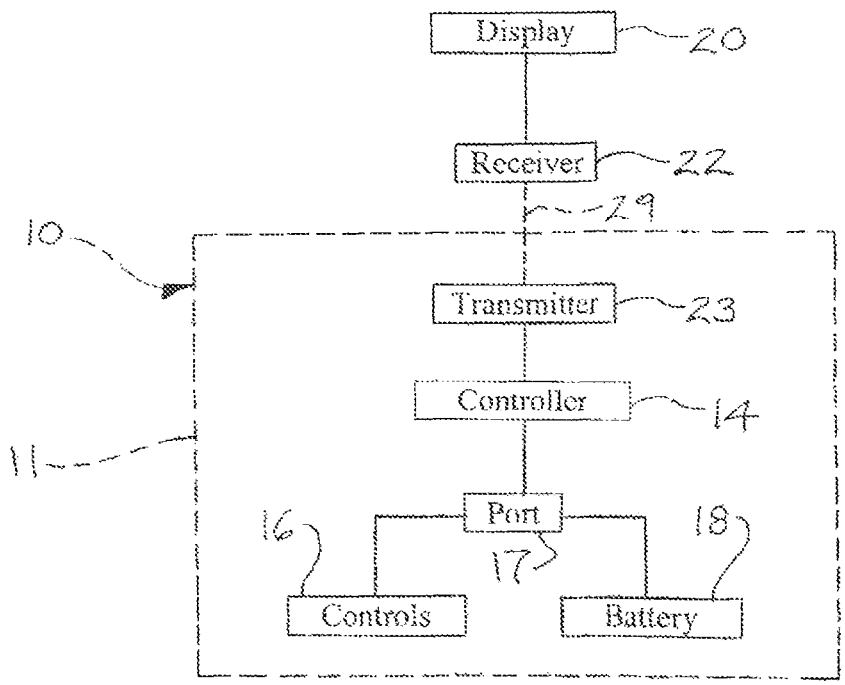
FIG. 9A is a block diagram of an alternative exemplary control module and a display wirelessly connected to the control module according to an illustrative embodiment of the prosthetic devices with electronic display.

As illustrated in FIG. 9A of the drawings, in some embodiments of the control module 10, a transmitter 23 may interface with the controller 14. A receiver 22 may interface with the display 20. The transmitter 23 communicates with the receiver 22 through wireless signals 29. Accordingly, the controller 14 is adapted to transmit image and/or video data to the display 20 via the transmitter 23, wireless signals 29 and receiver 22.

Figure 2:
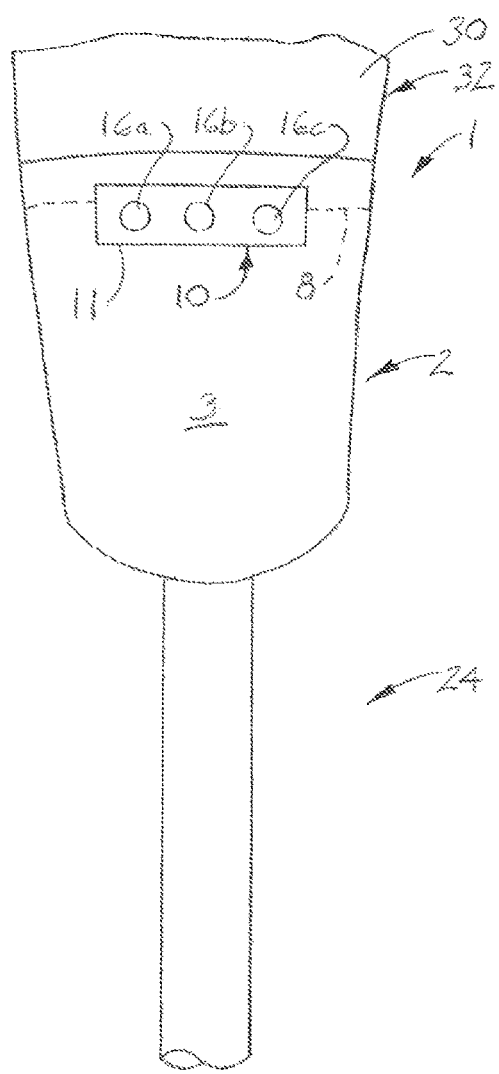
FIG. 2 is a rear view, partially in section, of the illustrative prosthetic device with electronic display illustrated in FIG. 1.

As illustrated in FIG. 2, in some embodiments, the display controls 16 for the image 21 on the display 20 may include a power switch 16a which controls flow of electrical current from the battery 18 (FIG. 9) to the display 20; a blink control switch 16b which facilitates selective blinking of the image or images 21 on the display 20; and/or a dimmer switch 16c which facilitates selective dimming and brightening of the image or images 21 on the display 20.

In application of the prosthetic device 1, the upper leg portion 2 receives the residual limb 30 of the wearer 32. The wearer 32 can selectively display one or more of the selected images 21 on the display 20 by appropriate manipulation of the display controls 16 (FIG. 9) on the control module 10. For example and without limitation, the wearer 32 may selectively turn the display 20 on and off by manipulation of the power switch 16a (FIG. 2); control blinking of the images 21 on the display 20 by manipulation of the blink control switch 16b; and control the brightness or the images 21 by manipulation of the dimmer switch 16c. Accordingly, as the wearer 32 dons the prosthetic device 1, the images 21 on the display 20 provide a means of self-expression to observers. Additionally or alternatively, the images 21 on the display 20 may provide a means of displaying information and/or variables measured by the controller 14 and/or sensors (not illustrated) such as temperature sensors, for example and without limitation, which may interface with the controller 14 in some embodiments.

It will be recognized and understood that the prosthetic device 1 is equally applicable and adaptable to alternative prosthetic device designs which are known by those skilled in the art. For example and without limitation, in some embodiments the prosthetic device 1 may include a covering portion (not illustrated) which receives the upper leg portion or a remaining portion of the residual limb 30 of the wearer 32 according to the knowledge of those skilled in the art. The covering portion (not illustrated) may include the display 20, wiring 8 and control module 10 and/or other functional components.

Figure 7:
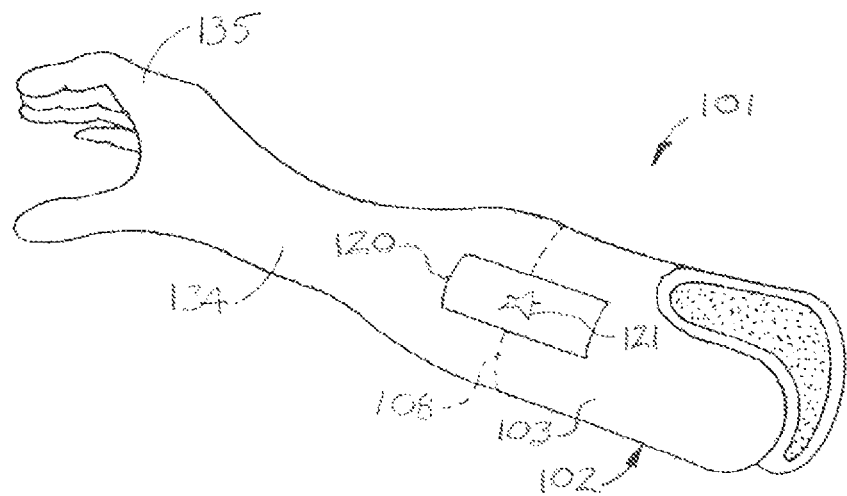
FIG. 7 is a perspective view of an illustrative arm embodiment of the prosthetic devices with electronic display.
Figure 8:
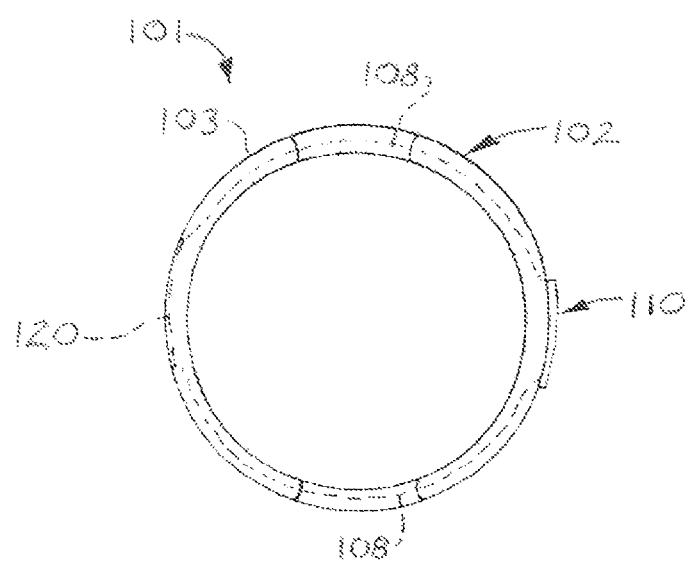
FIG. 8 is a rear view of the illustrative arm embodiment of the prosthetic device with electronic display illustrated in FIG. 7.

Referring next to FIGS. 7 and 8 of the drawings, an illustrative arm embodiment of the prosthetic devices with electronic display is generally indicated by reference numeral 101. In FIGS. 7 and 8, elements which are analogous to the respective elements of the prosthetic device 1 which was heretofore described with respect to FIGS. 1-6 are designated by the same reference numeral in the 100 series. The prosthetic device 101 may include an arm, or alternatively, forearm portion 102 which is adapted to be fitted on the residual arm or residual forearm (not illustrated) of a wearer to replace a portion or most of the wearer's natural arm which was lost or is missing due to injury, illness, or congenital deformity, for example. In some embodiments, a wrist portion 134 having a hand 135 may extend from the forearm portion 102. At least one display 120 may be provided on the exterior surface of the forearm portion 102, as illustrated, and/or on the forearm portion 134. As illustrated in FIG. 8, a control module 110 may be provided on the exterior surface of the forearm portion 102 and/or the wrist portion 134. The control module 110 may be electrically connected in the display 120 via control wiring 108, which may extend through a wiring space (not illustrated) or may otherwise be embedded in the prosthesis wall 103 as was heretofore described with respect to the prosthetic device 1. Operation of the display 120 of the prosthetic device 101 may be as was heretofore described with respect to the prosthetic device 1 in FIGS. 1-6. In some embodiments, the control module 110 and the display 120 may be retrofitted in an existing prosthetic device 101 according to the knowledge of those skilled in the art.

Figure 8A:
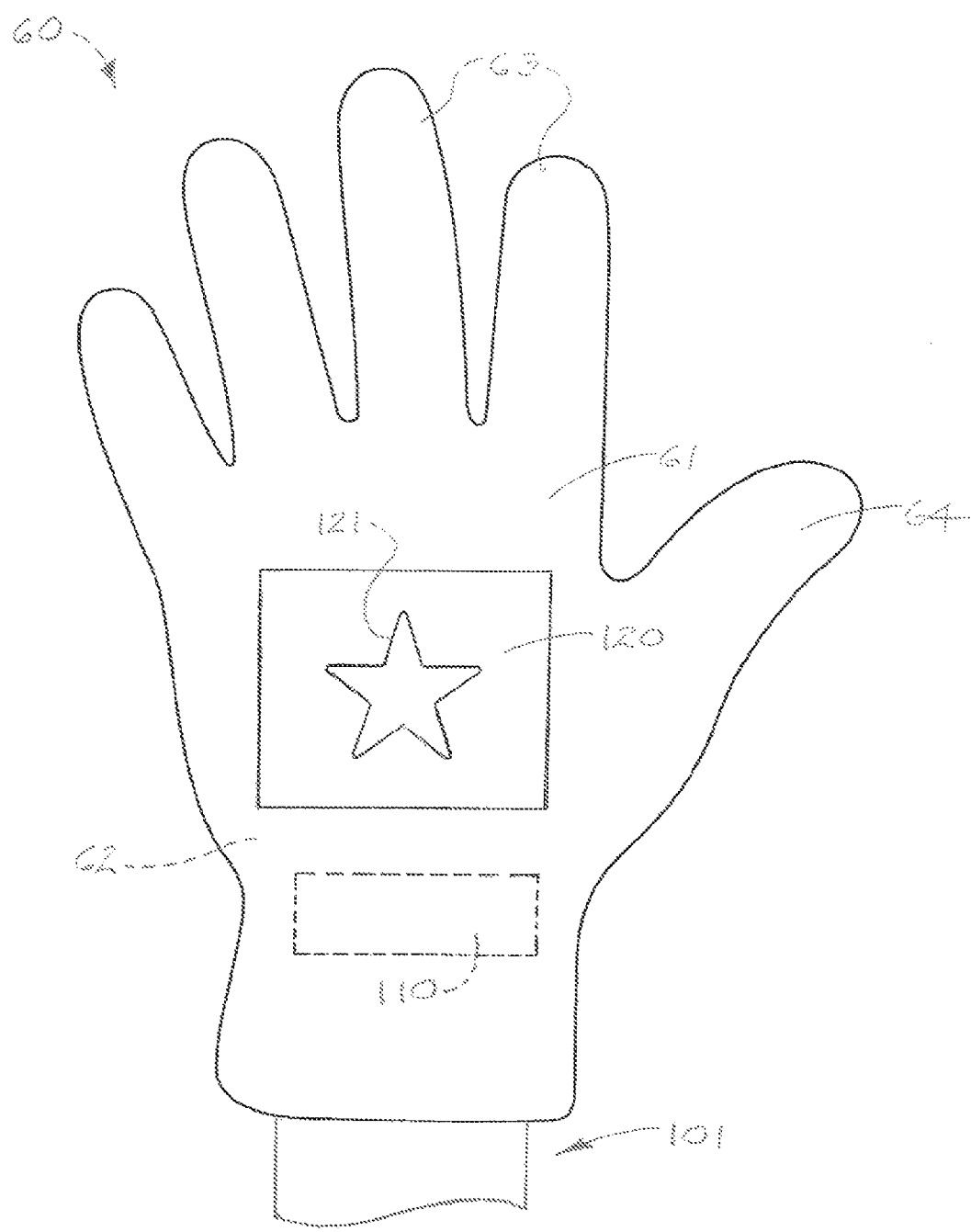
FIG. 8A is a rear view of an exemplary cosmetic prosthesis glove according to an illustrative embodiment of the prosthetic device with electronic display.

Referring next to FIG. 8A of the drawings, an exemplary cosmetic prosthetic glove according to an illustrative embodiment of the prosthetic device with electronic display, hereinafter glove, is generally indicated by reference numeral 60. The glove 60 may be adapted to be fitted over a prosthetic device such as the prosthetic device 101 which was heretofore described with respect to FIGS. 7 and 8, for example and without limitation, for cosmetic purposes. The glove 60 may include a backhand glove surface 61, a palm glove surface 62, glove fingers 63 and a glove thumb 64. A control module 110 and a display 120 may be provided at selected positions on the glove 60. In some embodiments, the display 120 may be provided on the backhand glove surface 61 and the control module 110 may be provided on the palm glove surface 62, as illustrated. In other embodiments, the positions of the control module 110 and the display 120 may be reversed or may both be provided on the backhand glove surface 61 or the palm glove surface 62. The glove 60 is adapted to be placed on the prosthetic device 101 typically for cosmetic purposes, as is known by those skilled in the art. The control module 110 may be operated to present at least one image 121 on the display 120, as was heretofore described.

Figure 10:
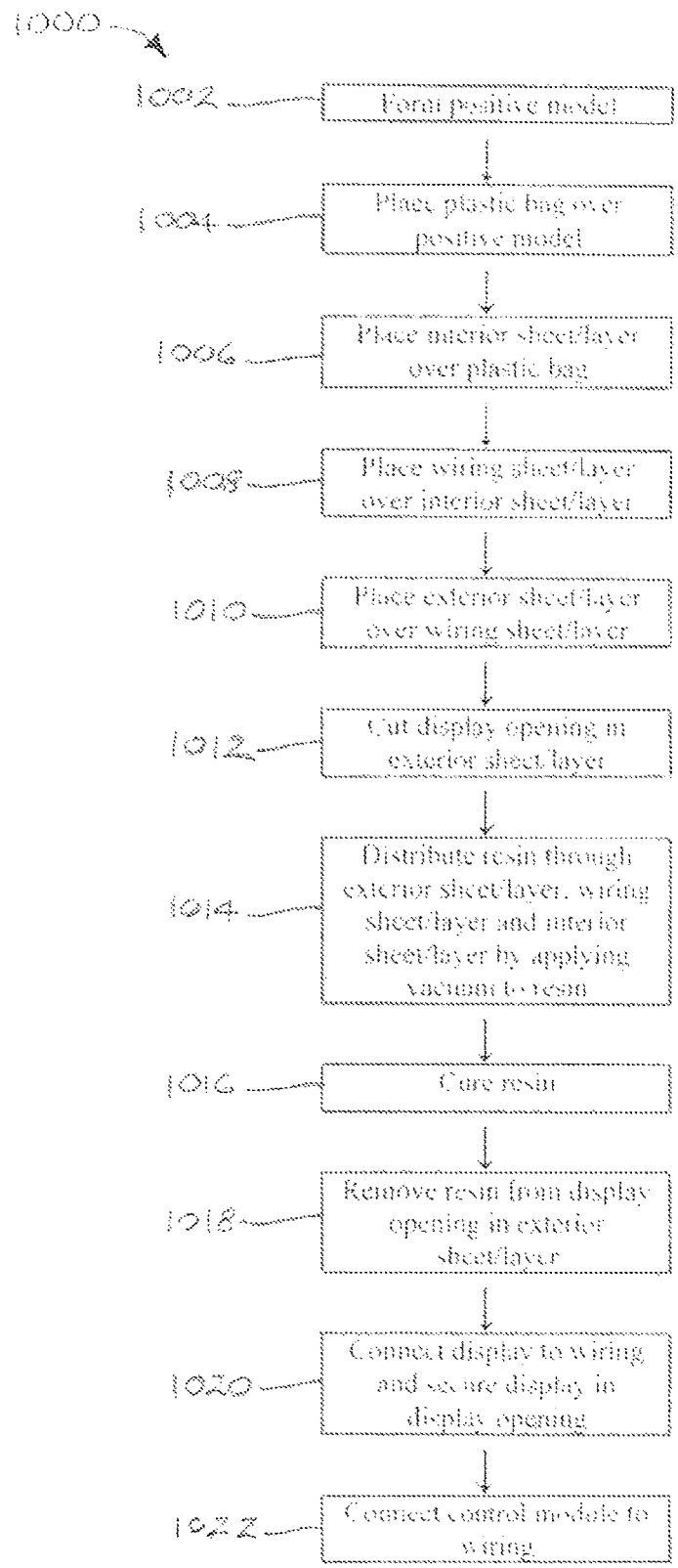
FIG. 10 is a flow diagram of an illustrative embodiment of a method of fabricating a prosthetic device with electronic display.

Referring next to FIG. 10, a flow diagram of an illustrative embodiment of an exemplary method of fabricating a prosthetic device with electronic display is generally indicated by reference numeral 1000. In block 1002, a positive model may be formed. The positive model may be an arm cast or a leg cast. In block 1004, a plastic bag may be placed over the positive model and secured. In block 1006, an interior sheet/layer may be placed over the plastic bag. The interior sheet/layer may include a woven sheet or layer of material such as fiberglass or carbon fiber, for example and without limitation. In block 1008, a wiring sheet/layer in which control wiring is embedded may be placed over the interior sheet/layer. In block 1010, an exterior sheet/layer may be placed over the wiring sheet/layer. The exterior sheet/layer may be similar in construction to the interior sheet/layer. In block 1012, a display opening may be cut in the exterior sheet/layer. In block 1014, resin may be distributed through the exterior sheet/layer, the wiring sheet/layer and the interior sheet/layer by application of vacuum to the resin. In block 1016, the resin may be cured using conventional resin curing techniques.

In block 1018, cured resin may be cut and/or otherwise removed from the display opening in the exterior sheet/layer. In block 1020, a display may be connected to control wiring in the wiring sheet/layer and secured in the display opening. In block 1022, a control module may be connected to the control wiring in the wiring sheet/layer. The control module may be attached to the prosthetic device using suitable attachment techniques.

It will be appreciated by those skilled in the art that the prosthetic devices of the disclosure are amenable to a variety of embodiments. For example and without limitation, referring again to FIG. 3, in some embodiments, the control module 10 may be inserted inside the upper leg portion 2 and may be secured therein using magnets, clips, clamps and/or other attachment technique. In other embodiments, the control module 10 may be attached to the exterior surface or the prosthesis wall 3 using a suitable attachment technique.

In some embodiments, an inner transparent or translucent layer or sheet of plastic may be thermoformed on a positive model of the leg. One or more electroluminescent wires and/or panels may be placed against the inner layer or sheet and arranged in the form of a squiggle, line, logo or pattern, for example and without limitation. An outer transparent or translucent layer or sheet of plastic or clear protective coating may be thermoformed on the inner layer or sheet with the electroluminescent wires or panels sandwiched between the sheets or layers. The electroluminescent wires or panels may be connected to the control module 10 to facilitate flow of electrical current through the electroluminescent wires or panels to illuminate the wires and the pattern which is formed by the wires or panels.

Figure 10A:
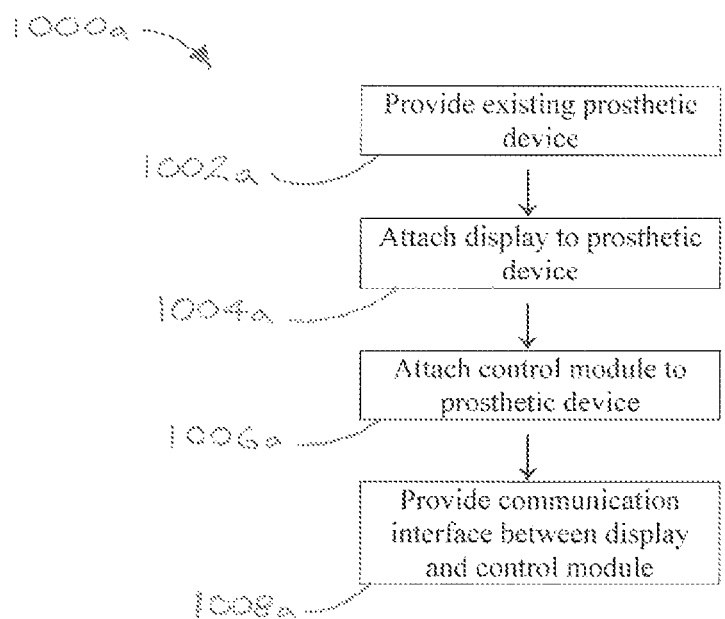
FIG. 10A is a flow diagram of an illustrative embodiment of a method of retrofitting an electronic display and control module to an existing prosthetic device.

Referring next to FIG. 10A of the drawings, a flow diagram of an illustrative embodiment of a method of retrofitting an electronic display and control module to an existing prosthetic device is generally indicated by reference numeral 1000a. In block 1002a, an existing prosthetic device is provided. In some embodiments, the prosthetic device may be adapted to be fitted on a residual limb corresponding to an upper or lower leg of a wearer. In other embodiments, the prosthetic device may be adapted to be fitted on a residual limb corresponding to an upper or lower arm of a wearer. In block 1004a, a display is attached to the prosthetic device. In block 1006a, a control module is attached to the prosthetic device. In block 1008a, a communication interface is provided between the display and the control module. In some embodiments, the communication interface may include wiring or other electrical communication pathway or contact. In other embodiments, the communication interface may include a wireless interface.

Figure 11:
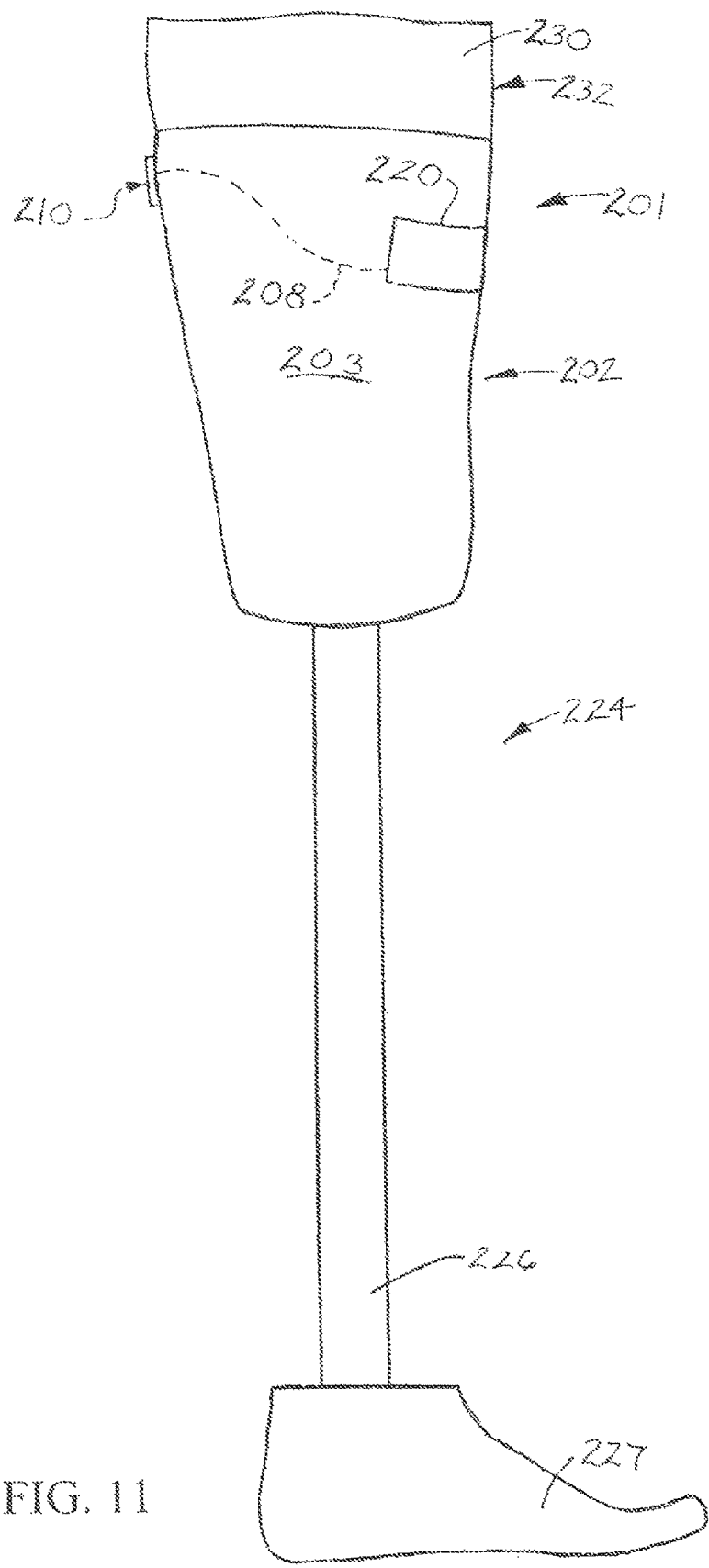
FIG. 11 a side view of an alternative illustrative leg embodiment of the prosthetic devices with electronic display, fitted on the leg of a wearer (illustrated in section)

Referring next to FIGS. 11 and 12 of the drawings, an alternative illustrative embodiment of the prosthetic devices with electronic display is generally indicated by reference numeral 201. In the prosthetic device 201, elements which are analogous to the respective elements of the prosthetic device 1 that was heretofore described with respect to FIGS. 1-9A are designated by the same numeral in the 201-299 series in FIGS. 11 and 12. While the prosthetic device 201 in FIG. 11. is presented as a leg embodiment, in other embodiments the prosthetic device 201 may be an arm embodiment as was heretofore described with respect to FIG. 7.

The prosthetic device 201 may include an electroluminescent lamp (EL) display 220. As illustrated in FIG. 12, the EL display 220 may include an encapsulant layer 240. The encapsulant layer 240 may include a protective encapsulant such as clear coat, for example and without limitation. In some embodiments, the encapsulant layer 240 may include UV cure ink 5018/A/G or solvent-based 7165 which is available from the DuPont Corp. (www.dupont.com). In some embodiments, the encapsulant layer 240 may be attached to the exterior surface of the prosthesis wall 203 of the prosthetic device 201 using bonding techniques known by those skilled in the art. In other embodiments, the encapsulant layer 240 may be provided within a cavity or void (not illustrated) in the exterior surface of the prosthesis wall 203. In some embodiments, the encapsulant layer 240 may be laminated within the prosthesis wall 203 of the prosthetic device 201 according to the knowledge of those skilled in the art.

In some embodiments, 5018/A/G screen printable UV cure inks or 7165 solvent ink, both available from DuPont Corp., may be used as the encapsulant layer 240 in order to provide electrical insulation and extra protection of the components of the prosthetic device 201 against humid environments. The UV encapsulants may not adhere well to ITO-sputtered film, so in some embodiments it may be desirable to limit the print area of the 5018/A/G to that of the underlying dielectric layer 242. 7165 solvent ink adheres well to ITO film but may only be usable in a single print. In more complex embodiments of the EL display 220, two layers of 5018/A/G may be used as an effective insulator in the encapsulant layer 240 where conductor crossovers are present. It may be desirable to print the first UV encapsulant layer over the entire lamp area to prevent cracking over the dielectric where local crossovers are printed. In some embodiments, a thick, single print of 7165 solvent ink encapsulant may be used as an option.

A rear electrode 241 may be provided on the encapsulant layer 240. The rear electrode 241 may include any electrically-conductive material which is suitable for the purpose. In some embodiments, the rear electrode 241 may include 9145 silver and/or 8144 carbon which is available from the DuPont Corp., for example and without limitation. At least one dielectric layer 242 may be provided on the rear electrode 241. In some embodiments, at least two prints of dielectric layers 242 (<25 microns total dried thickness) may be provided over the rear electrode 241. In some embodiments, at least three prints of dielectric layers 242 (>25 microns total dried thickness) may be provided over the rear electrode 241 for optimum yield and reliability. A phosphor layer 243 may be provided on the dielectric layer or layers 242. The phosphor layer 243 may include an inorganic phosphor such as a zinc sulfide compound, for example and without limitation. The phosphor particles of the phosphor layer 243 may be selected and arranged to define at least one desired pattern, image or symbol on the EL display 220 in application of the prosthetic device 201 which will be hereinafter described.

A front electrode 244 is provided in electrical contact with the rear electrode 241 through an AC voltage power source 248 and bus bar 249. The front electrode 244 may include any electrically-conductive material which is suitable for the purpose. In some embodiments, the front electrode 244 may include translucent conductor 7162 which has ATO (antimony-doped tin oxide) and is available from the DuPont Corp.

In EL display designs with small-lit areas, screen-printable translucent conductive ink may be used as the front electrode 244. The as-printed resistivity of translucent conductors can be around 100 times that of ITO film. Consequently, lit areas should be kept small so that good uniformity of illumination is achieved. EL displays 220 may be fabricated with an area of 10 cm ×5 cm without noticeable darkening towards the center of the displays (powered at 100V/400 Hz). Higher frequency operations may cause darkening towards the center of the displays; thus. use of frequencies below about 800 Hz may be optimum in some embodiments.

The bus bar 249 may include a printed electrically-conductive material such as silver, for example and without limitation. It may be desirable to print a silver bus bar close to the lit area around the perimeter of the translucent conductor front electrode 244. This expedient may improve the light uniformity by lowering the contact resistance and minimizing the voltage drop across the surface of the front electrode 244 instead of using a carbon electrode. A printed silver bus bar 249 along the perimeter of the El display 220 may be used for large areas in order to provided more even illumination of the EL display 220.

A base substrate layer 245 may be provided on the phosphor layer 243. In some embodiments, the base substrate layer 245 may include polyester film sputtered with ITO (Indium Tin Oxide) or coated with an electrically-conductive polymer or other suitable material.

Accordingly, the base substrate layer 245 may be obtained with an ITO transparent conductor sputter-coated on one side. Polyester thickness of between 100-175 μm and resistivities ranging from 50 to 300 Ω/sq can be used. Heat-stabilized film may be recommended as drying temperatures of up to 130 degrees C. may be used in some fabrication methods. Non-ITO coated films may be used for high resistivity applications (from about 1000 Ω/sq to about 3000 Ω/sq). In some embodiments, the base substrate layer 245 may include a screen-printed conducting translucent ink on a clear base substrate. In other embodiments, the base substrate layer 245 may include heat-stabilized, print-treated polyester. In still other embodiments, the base substrate layer 245 may include any material or combination of materials which is consistent with the functional requirements of the base substrate layer 245 in the EL display 220.

It will be recognized and understood that the encapsulant layer 240, the rear electrode 241, the dielectric layer or layers 242, the phosphor layer 243, the front electrode 244 and the base substrate layer 245 can be applied using any technique which is known by those skilled in the art and is consistent with the material of construction of each layer. These application techniques include but are not limited to silk screening, screen printing and spraying, for example and without limitation.

The controller 14 (FIG. 9) of the control module 210 may communicate with the bus bar 249 of the through control wiring 208 (FIG. 11) as was heretofore described with respect to FIG. 9. Alternatively, the controller 14 may communicate with the bus bar 249 through a transmitter 23, wireless signals 29 and a receiver 22 as was heretofore described with respect to FIG. 9A. Accordingly, operation of the control module 210 establishes flow of electrical current between the rear electrode 241 and the front electrode 244 of the EL display 220. Application of an AC voltage across the rear electrode 241 and the front electrode 244 generates a changing electric field within the phosphor particles of the phosphor layer 243, causing the phosphor particles to emit light 250 through the base substrate layer 245. The phosphor particles in the phosphor layer 243 may be selected by color and arranged in position to emit light 250 of different wavelengths and form at least one selected light pattern or image. In some embodiments, an inverter (DC-AC converter) may be used as the power source 248. The inverter may generate 60~115V and frequencies in the region of about 50~1000 Hz. For signage applications, much higher frequencies can be used to increase the brightness of the EL display 220.

Output of the light 250 from the EL display 220 may gradually decay with time as the luminescent efficiency decreases. The presence of any moisture in the phosphor layer 243 may accelerate this decline. The phosphor particles used in the phosphor layer 243 may be micro-encapsulated to hinder the penetration of moisture and thus, prolong the useful life of the EL display 220.

Application of the prosthetic device 201 may be as was heretofore described with respect to the prosthetic device 1 in FIGS. 1-9A. The control module 210 can be selectively operated to facilitate emission of light 250 from the EL display 220 to form at least one selected single-color or multi-colored image which may be defined by the pattern of phosphor particles in the phosphor layer 243.

Referring next to FIGS. 13-17 of the drawings, an exemplary sequential fabrication technique for the EL display 220 is illustrated. In FIG. 13, a front electrode 244 may be provided over a base substrate layer 245 (FIG. 12). In FIG. 14, a phosphor layer 243 may be provided over the front electrode 244. In FIG. 15, at least one dielectric layer 242 may be provided over the phosphor layer 243. In FIG. 16, a rear electrode 241 may be provided over the dielectric layer or layers 242. A bus bar 249 may connect the rear electrode 241 to the front electrode 244. In FIG. 17, an encapsulant layer 240 may be provided over the rear electrode 241. A power source 248 (FIG. 12) may be electrically connected to the bus bar 249. The power source 248 of the EL display 220 may interface with the control module 210 (FIG. 11) as was heretofore described with respect to FIG. 9 or FIG. 9A.

Figure 24:
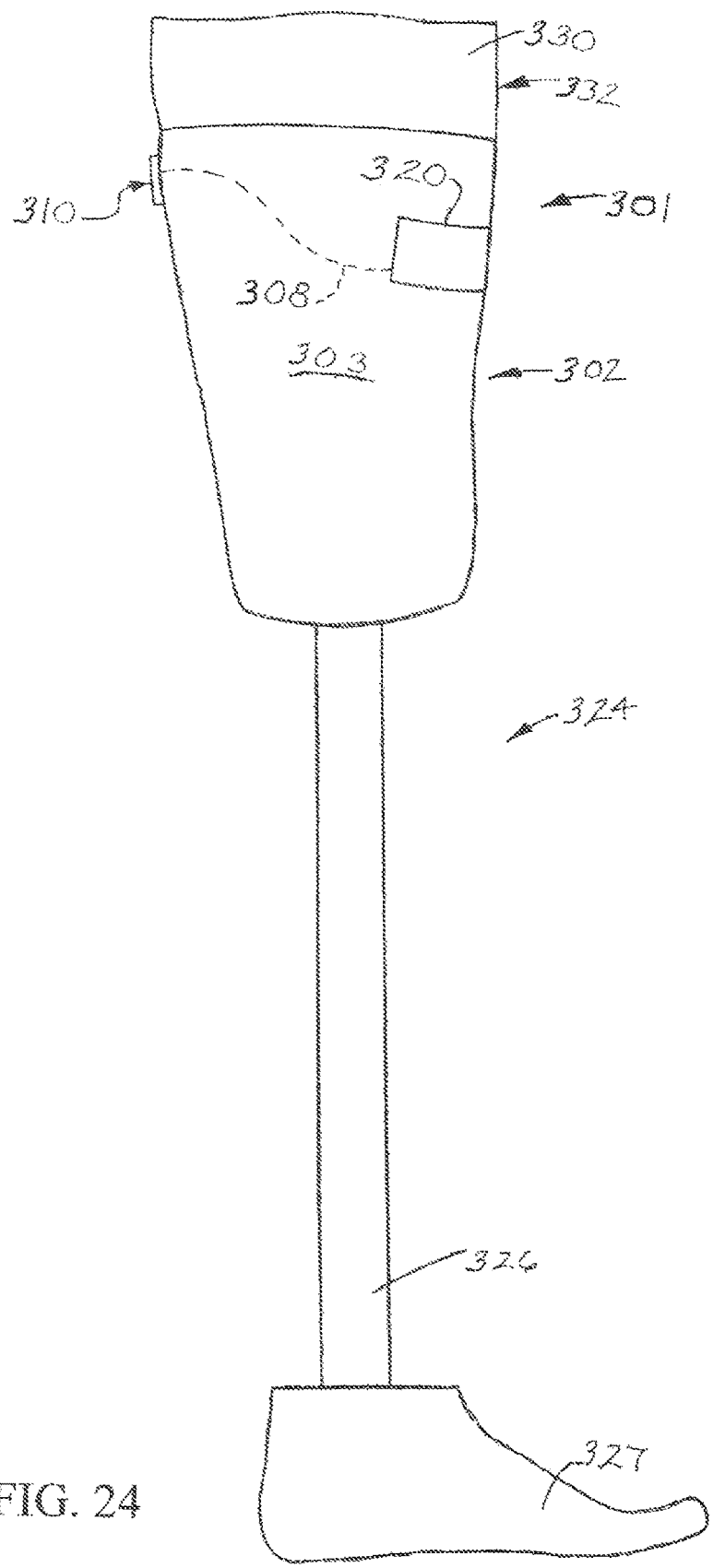
FIG. 24 is a side view of an alternative illustrative leg embodiment of the prosthetic devices with electronic display, fitted on the leg (illustrated in section) of a wearer.

Referring next to FIGS. 18 and 24 of the drawings, an alternative illustrative embodiment of the prosthetic devices with electronic display is generally indicated by reference numeral 301 in FIG. 24. In the prosthetic device 301, elements which are analogous to the respective elements of the prosthetic device 201 that was heretofore described with respect to FIG. 11 are designated by the same numeral in the 301-399 series in FIGS. 18 and 24. While the prosthetic device 301 in FIG. 18 is presented as a leg embodiment, in other embodiments the prosthetic device 301 may be an arm embodiment as was heretofore described with respect to FIG. 7.

The prosthetic device 301 may include an electroluminescent lamp (EL) display 320. As illustrated in FIG. 18, the EL display 320 may include an encapsulant layer 340. In some embodiments, the encapsulant layer 340 may be attached to the exterior surface of the prosthesis wall 303 of the prosthetic device 301 using bonding techniques known by those skilled in the art. In other embodiments, the encapsulant layer 340 may be provided within a cavity or void (not illustrated) in the exterior surface of the prosthesis wall 303. In some embodiments, the encapsulant layer 340 may be laminated within the prosthesis wall 303 of the prosthetic device 301 according to the knowledge of those skilled in the art.

A rear electrode 341 may be provided on the encapsulant layer 340. At least one dielectric layer 342 may be provided on the rear electrode 341. A phosphor layer 343 may be provided on the dielectric layer or layers 342. A front electrode 344 is provided in electrical contact with the rear electrode 341 through an AC voltage power source 348 and bus bar 349. A base substrate layer 345 may be provided on the phosphor layer 343. The encapsulant layer 340, the rear electrode 341, the dielectric layer or layers 342, the phosphor layer 343, the front electrode 344 and the base substrate layer 345 may have the same materials of construction as those respective components in the EL display 220 heretofore described with respect to FIG. 12.

The controller 14 (FIG. 9) of the control module may communicate with the bus bar 349 of the through control wiring 308 (FIG. 24) as was heretofore described with respect to FIG. 9. Alternatively, the controller 14 may communicate with the bus bar 349 through a transmitter 23, wireless signals 29 and a receiver 22 as was heretofore described with respect to FIG. 9A.

Referring next to FIGS. 19-23 of the drawings, an exemplary sequential fabrication technique for the EL display 320 is illustrated. In FIG. 19, an encapsulant layer 340 is provided. In some embodiments, the encapsulant layer 340 may be part of the prosthesis wall 303 of a prosthetic device. In other embodiments, the encapsulant layer 340 may be attached to the exterior surface of the prosthesis wall 303 or may be provided in a cavity or void (not illustrated) in the exterior surface of the prosthesis wall 303. The encapsulant layer 340 may be applied to the prosthesis wall 303 as a translucent conductive ink, although alternative substrate types and materials may be used. In FIG. 20, a rear electrode 341 and bus bar 349 may be provided on the encapsulant layer 340. In FIG. 21, at least one dielectric layer 342 may be provided on the rear electrode 341. In FIG. 22, a phosphor layer 343 may be provided on the dielectric layer or layers 342. In FIG. 23, a base substrate layer 345 may be provided over the phosphor layer 343.

Application of the prosthetic device 301 may be as was heretofore described with respect to the prosthetic device 301 in FIGS. 1-9A. The control module 310 can be selectively operated to facilitate emission of light 350 from the EL display 320 to form a selected single-color or multi-colored image which is defined by the pattern of phosphor particles in the phosphor layer 343.

While the embodiments of the disclosure have been described above, it will be recognized and understood that various modifications can be made and the appended claims are intended to cover all such modifications which may fall within the spirit and scope of the disclosure.

What is claimed is:

1. A prosthetic device, comprising:
    an upper leg portion having a lamination forming a multi-layered prosthesis wall with an exterior surface having a convex curvature, the prosthesis wall sized and configured to receive a residual limb of a wearer, the prosthesis wall including an outer wall layer, an inner wall layer, a display cavity in the outer wall layer and a coating layer on the outer wall layer;
    at least one electroluminescent display in the display cavity, the at least one electroluminescent display embedded in the lamination of the prosthesis wall with the coating layer coating the at least one display;
    a control module embedded in the lamination of the prosthesis wall in spaced-apart relationship to the at least one display and interfacing with the at least one display, the control module adapted to present at least one of at least one image and video on the at least one display, the control module having a control module housing with a concave surface generally complementary to the convex curvature of the exterior surface of the prosthesis wall;
    at least one port provided on the control module; and
    a lower leg portion extending from the upper leg portion, the lower leg portion having a foot portion configured to correspond functionally to a foot of the wearer.

2. The prosthetic device of claim 1 further comprising control wiring embedded in the prosthesis wall and electrically connecting the at least one display to the control module.

3. The prosthetic device of claim 1 wherein the control module interfaces with the at least one display wirelessly.

4. The prosthetic device of claim 1 wherein the control module comprises a power switch, a blink control switch and a dimmer switch.

5. A prosthetic device, comprising:
    a forearm portion configured to be fitted on a residual arm of a wearer;
    a wrist portion having a hand extending from the forearm portion;
    a multi-layered prosthesis wall with an exterior surface having a convex curvature, the prosthesis wall forming a lamination having a front wall portion and a rear wall portion forming the forearm portion and the wrist portion, the prosthesis wall including an outer wall layer, an inner wall layer, a display cavity in the outer wall layer and a coating layer on the outer wall layer;
    at least one electroluminescent display in the display cavity, the at least one electroluminescent display embedded in the lamination of the front wall portion of the prosthesis wall with the coating layer coating the at least one electroluminescent display;
    a control module embedded in the lamination of the rear wall portion of the prosthesis wall and interfacing with the at least one display, the control module in an accessible location for selective manipulation by a user and adapted to present at least one of at least one image and video on the at least one display, the control module having a control module housing with a concave surface generally complementary to the convex curvature of the exterior surface of the prosthesis wall; and
    at least one port provided on the control module.

6. The prosthetic device of claim 5 wherein the display and the control module are embedded in the forearm portion.

7. The prosthetic device of claim 5 further comprising control wiring embedded in the prosthesis wall and electrically connecting the at least one display to the control module.

8. The prosthetic device of claim 5 wherein the control module interfaces with the at least one display wirelessly.

* * * * *